United States Patent
Matsumaru

(10) Patent No.: US 10,231,610 B2
(45) Date of Patent: Mar. 19, 2019

(54) ELECTRONIC ENDOSCOPE APPARATUS AND ELECTRONIC ENDOSCOPE SYSTEM

(71) Applicant: FUJIFILM Corporation, Tokyo (JP)

(72) Inventor: Yasushi Matsumaru, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 80 days.

(21) Appl. No.: 15/154,577

(22) Filed: May 13, 2016

(65) Prior Publication Data

US 2016/0278624 A1   Sep. 29, 2016

Related U.S. Application Data

(63) Continuation of application No. 13/545,655, filed on Jul. 10, 2012, now abandoned.

(30) Foreign Application Priority Data

Jul. 26, 2011 (JP) .................................. 2011-163494

(51) Int. Cl.
*A61B 1/00* (2006.01)
*A61B 1/12* (2006.01)
(Continued)

(52) U.S. Cl.
CPC .......... *A61B 1/128* (2013.01); *A61B 1/00009* (2013.01); *A61B 1/00011* (2013.01);
(Continued)

(58) Field of Classification Search
CPC ....... A61B 1/12; A61B 1/128; H04N 5/23241
See application file for complete search history.

(56) References Cited

U.S. PATENT DOCUMENTS

| 4,868,815 A | 9/1989 | Iwamura et al. |
| 2004/0193010 A1 | 9/2004 | Fujimori et al. |

(Continued)

FOREIGN PATENT DOCUMENTS

| JP | 7-194531 A | 8/1995 |
| JP | 2004-298241 A | 10/2004 |

OTHER PUBLICATIONS

Human translation of JP H07-194531.*
Notice of First Office Action issued in corresponding Chinese Application No. 2012102323338 dated Jan. 12, 2015.

*Primary Examiner* — Alexandra L Newton
(74) *Attorney, Agent, or Firm* — Birch, Stewart, Kolasch & Birch, LLP

(57) ABSTRACT

Electric power of a required voltage is supplied to an endoscope distal end portion, and a distal end temperature is prevented from being higher. An imaging device having an imaging element, and its peripheral circuit and a first circuit part including a first regulator as a power circuit are built in the endoscope distal end portion. The first circuit part is connected to a second circuit part via a cable. The second circuit part includes a second regulator supplying electric power to the first regulator. By the overcurrent detection function of a temperature detecting unit or a regulator arranged, when at least one abnormality of a temperature abnormality and an overcurrent in the distal end portion is detected, the output of at least one of the first regulator and the second regulator is stopped, and supply of power to the distal end portion is stopped.

10 Claims, 10 Drawing Sheets

(51) Int. Cl.
    *A61B 1/05* (2006.01)
    *A61B 1/06* (2006.01)
(52) U.S. Cl.
    CPC ............ *A61B 1/00027* (2013.01); *A61B 1/05* (2013.01); *A61B 1/0676* (2013.01)

(56) References Cited

U.S. PATENT DOCUMENTS

| | | | |
|---|---|---|---|
| 2006/0114986 A1* | 6/2006 | Knapp, II | A61B 1/00103 375/240.01 |
| 2007/0078304 A1 | 4/2007 | Shimizu et al. | |
| 2011/0031946 A1 | 2/2011 | Egan et al. | |

* cited by examiner

ELECTRONIC ENDOSCOPE APPARATUS AND ELECTRONIC ENDOSCOPE SYSTEM

CROSS-REFERENCE TO RELATED APPLICATIONS

The present application claims priority under 35 U.S.C. § 119 to Japanese Patent Application No. 2011-163494, filed on Jul. 26, 2011, all of which are hereby expressly incorporated by reference into the present application. The present application is Continuation Application based on the U.S. patent application Ser. No. 13/545,655.

BACKGROUND OF THE INVENTION

1. Field of the Invention

The present invention relates to an electronic endoscope apparatus and an electronic endoscope system, and particularly, to a management technique when an abnormality occurs in a distal end portion of the electronic endoscope in which an imaging device having a solid-state imaging element is built.

2. Description of the Related Art

Electronic endoscope systems used in the medical field or the like are constituted by an electronic endoscope (scope) in which an imaging device including a solid-state imaging element is provided at a distal end portion of an insertion part to be inserted into a subject to be examined, and a processor device that controls the operation of the imaging device, and performs various kinds of signal processing on imaging signals output from the imaging device to display an endoscope image on a monitor (display device).

Inside the distal end of the endoscope insertion part, temperature is apt to rise due to heat generation of the solid-state imaging element, heat generation caused by the loss of the light intensity of a light guide, or the like. If the internal temperature of the endoscope insertion part rises, the noise of the image signals increases and the image quality deteriorates. Additionally, due to a failure of a circuit in the distal end portion etc., overcurrent may flow and heat may be generated. Moreover, if the image signals from the distal end portion are no longer normally sent to the processor device, it is determined to be a dark image, and a control is made in a direction in which an iris (diaphragm mechanism) of a light source device is automatically opened such that the exposure quantity that is required is obtained. If a maximum quantity of light continues being emitted with the iris opened, the distal end portion further generates heat.

Since heat damage may be caused in a human body tissue if the temperature of the endoscope distal end portion reaches a high temperature, it is desired to maintain the temperature of the distal end portion below a certain fixed temperature.

JP1995-194531A (JP-H07-194531) suggests an electronic endoscope apparatus in which temperature detection means is arranged near a solid-state imaging element provided at the distal end of a scope, and when a temperature rise near the solid-state imaging element is detected due to generation of an overcurrent, the control of attenuating or cutting off supply of a driving signal to the solid-state imaging element or waveform shaping means is performed.

Additionally, a capsule endoscope disclosed in JP2004-298241A includes temperature detection means that detects internal temperature, and power source control means that performs the control of stopping supply of power to an internal electric circuit in a case where the internal temperature exceeds a predetermined value.

SUMMARY OF THE INVENTION

A plurality of types of scopes, such as a scope for observation of the stomach and a scope for observation of the small intestine, exist corresponding to applications and observation purposes in the electronic endoscope. Construction of systems that can commonly use the same processor device and the same light source device is desired for these various types of scopes. Wiring lines used for the connection between the electronic endoscope and the processor device are very thin (for example, AWG44 or the like), and the wiring line length (the length of the cable) is various depending on models. In a case where the influence of a voltage drop caused by a wiring portion that connects the endoscope distal end portion and the processor device is not negligible, and the type of scope is changed, means (mechanism) for supplying electric power of a required voltage to the scope distal end portion is required.

Moreover, as already described, maintenance of the temperature of the endoscope distal end portion below a certain fixed temperature is also required. If electric power of a voltage higher than needed is supplied to the endoscope distal end portion in anticipation of the voltage drop caused by the wiring portion, the amount of excess generates heat in the conversion to a predetermined voltage. Accordingly, it is desirable to suppress such excessive heat generation.

With respect to these problems, JP1995-194531A (JP-H07-194531) and JP2004-298241A do not present specific means (mechanism).

The present invention has been made in view of the above-mentioned problems and an object of the present invention is to provide an electronic endoscope apparatus and an electronic endoscope system that, even in a case where the type of scope is changed, can supply electric power of a required voltage to an endoscope distal end portion, can suppress heat generation of the distal end portion, and can prevent a distal end temperature from reaching a temperature higher than an allowable temperature.

In order to achieve the above object, an electronic endoscope apparatus of the invention includes: an imaging device built in a distal end portion of an endoscope insertion part, and having a solid-state imaging element that images a region to be observed; a first regulator arranged within the distal end portion along with the imaging device, and supplying electric power of a required voltage to the imaging device; a cable including signal lines that transmit signals obtained from the imaging device and a power supply line that supplies electric power to the first regulator; a second circuit part electrically connected to a first circuit part including the imaging device and the first regulator within the distal end portion via the cable; a second regulator mounted on the second circuit part and connected to the first regulator via the power supply line; an abnormality detecting unit that detects at least one abnormality of a temperature abnormality and an overcurrent in the distal end portion; and a power supply stop unit that stops the output from at least one regulator of the first regulator and the second regulator in a case where an abnormality is detected by the abnormality detecting unit.

According to the present invention, the regulators are respectively arranged at the first circuit part built in the endoscope distal end portion and the second circuit part connected to the first circuit part via the cable, and in a case where an abnormality of the distal end portion is detected, output operation of the first regulator or the second regulator or output operation of both the regulators is stopped, and supply of power to the imaging device of the distal end portion is stopped. This can suppress heat generation of the distal end portion. By stopping supply of power to the distal end portion by the abnormality detection, the abnormal state does not last for a long time, and a failure of an electronic circuit can be prevented.

Additionally, in the present invention, the regulators are arranged at both the first circuit part and the second circuit part, electric power is supplied to the regulator (first regulator) of the first circuit part from the regulator (second regulator) of the second circuit part, is converted into a voltage required of the first regulator, and is used as a power source of the imaging device. By adopting such a power supply system, electric power of a predetermined voltage can be stably supplied to the first regulator. In addition, the first regulator can output one type or a plurality of types (two or more types) of predetermined voltages.

A configuration is possible in which a temperature detecting unit is provided within the distal end portion as the abnormality detecting unit in the electronic endoscope apparatus of the present invention. The temperature detecting unit can also be integrated in the same semiconductor package as the imaging element, and can also be configured in a separate package.

As an aspect of the present invention, a configuration can be adopted in which the second circuit part includes a control circuit that controls the operation of the second regulator, and the control circuit provides a control signal stopping the output of the second regulator to the second regulator on the basis of a signal obtained from the abnormality detecting unit, thereby cutting off the supply of power from the second regulator.

For example, a configuration can be adopted in which a CPU (Central Processing Unit) is mounted on the second circuit part, and an enable signal that switches the operation/non-operation of the second regulator is given to the second regulator from the CPU.

As another aspect of the present invention, a configuration can be adopted in which at least one of the first regulator and the second regulator is provided with an overcurrent detecting circuit, and the overcurrent detecting circuit is used as the abnormality detecting unit.

An overcurrent detecting circuit of a regulator having an overcurrent protection function can be used for the abnormality detecting unit.

As still another aspect of the present invention, a configuration can be adopted in which the first regulator includes the overcurrent detecting circuit, and includes a self-shutdown circuit that stops output automatically in a case where overcurrent is detected, and a self-shutdown circuit built in the first regulator is used as the power supply stop unit.

A regulator having a self-shutdown function against an overcurrent functions also as the abnormality detecting unit and the power supply stop unit.

As a still further aspect of the present invention, a configuration can be adopted in which the second regulator includes the overcurrent detecting circuit, and includes a self-shutdown circuit that stops output automatically in a case where overcurrent is detected, and a self-shutdown circuit built in the second regulator is used as the power supply stop unit.

If an abnormality occurs in a circuit mounted on the distal end portion and an overcurrent flows, an electric current supplied from the second regulator also increases. Accordingly, an abnormality (overcurrent) of the distal end portion can be indirectly detected by adopting a regulator with an overcurrent protection function as the second regulator. Additionally, the output of the first regulator is also stopped by stopping the output of the second regulator.

As a still further aspect of the present invention, a configuration can be adopted in which the second circuit part includes a control circuit that controls the operation of the second regulator, the second regulator includes the overcurrent detecting circuit, a signal is sent to the control circuit if overcurrent is detected by the overcurrent detecting circuit, and the control circuit provides a control signal stopping the output of the second regulator to the second regulator on the basis of the signal, thereby cutting off the supply of power from the second regulator.

Even in a case where the second regulator is not provided with the self-shutdown circuit, the detection information of the overcurrent detecting circuit can be notified to the control circuit in the second circuit part, and the operation of the second regulator can be stopped via the control circuit.

As a still further aspect of the present invention, a configuration can be adopted in which the second circuit part is arranged at a connector portion formed at the end portion of the cable opposite to the first circuit part.

The second circuit part, which is electrically connected to the first circuit part through the cable, can be arranged at a place apart from the endoscope distal end portion. Although the arrangement place of a second circuit part is arbitrary, for example, an aspect is possible in which the second circuit part is arranged at a connector portion that couples the electronic endoscope apparatus and the light source device together, a connector portion that couples the electronic endoscope apparatus and the processor device together, the manipulating part of the electronic endoscope, or the like.

As a still further aspect of the present invention, the electronic endoscope apparatus preferably further includes a feedback circuit that returns an input voltage, which is supplied to the first regulator via the power supply line from the second regulator, to the second regulator.

According to this aspect, the influence of a voltage drop by the cable can be compensated for, and an input voltage to the first regulator can be maintained at a desired value. This can suppress wasteful heat generation in the case of voltage conversion by the first regulator.

In the present invention, a CMOS (Complementary Metal Oxide Semiconductor) type solid-state imaging element can be used for the solid-state imaging element.

As compared to a CCD (Charge Coupled Device) sensor, the CMOS type solid-state imaging element allows integration with a drive circuit and its peripheral circuit, and allows a small sensor module to be accommodated in the distal end portion.

For example, the imaging device is able to have a configuration including an A/D converter that converts voltage signals read from the solid-state imaging element into digital signals and a parallel/serial converter that converts imaging signals digitized by the A/D converter into serial signals from parallel signals.

In addition, an aspect is preferable in which an LVDS (Low Voltage Differential Signaling) transmission system that is not easily influenced by disturbance noise is adopted as a signal transmission system of imaging signals converted into serial signals.

Additionally, in order to achieve the above object, there is provided an electronic endoscope system including: an electronic endoscope apparatus having an imaging device, having a solid-state imaging element that images a region to be observed, built in a distal end portion of an endoscope insertion part; a processor device that performs signal processing on imaging signals output from the imaging device of the electronic endoscope apparatus; and a light source for illumination that generates illumination light to be irradiated to a region to be observed from an illumination window provided at a distal end face of the endoscope insertion part. The electronic endoscope apparatus includes: a first regulator arranged within the distal end portion along with the imaging device, and supplying electric power of a required voltage to the imaging device; a cable including signal lines that transmit signals obtained from the imaging device and a power supply line that supplies electric power to the first regulator; a second circuit part electrically connected to a first circuit part including the imaging device and the first regulator within the distal end portion via the cable; a second regulator mounted on the second circuit part and connected to the first regulator via the power supply line; an abnormality detecting unit that detects at least one abnormality of a temperature abnormality and an overcurrent in the distal end portion; and a power supply stop unit that stops the output from at least one regulator of the first regulator and the second regulator in a case where an abnormality is detected by the abnormality detecting unit.

Although a configuration is also possible in which the light source for illumination is arranged at the distal end portion of the endoscope insertion part, a configuration is adopted in which illumination light is guided to the distal end of the endoscope insertion part using an optical fiber or other light guides, in a case where a light source is installed outside.

As an aspect of the electronic endoscope system of the present invention, a configuration can be adopted in which the second circuit part is arranged at a connector portion that detachably couples together the electronic endoscope and the light source for illumination.

According to the present invention, electric power of a proper voltage can be supplied to the distal end portion of the endoscope insertion part, and a distal end temperature can be prevented from reaching a temperature higher than an allowable temperature.

DESCRIPTION OF THE PREFERRED EMBODIMENTS

Embodiments of the present invention will be described below in detail with reference to the accompanying drawings.

First Embodiment

Figure 1:
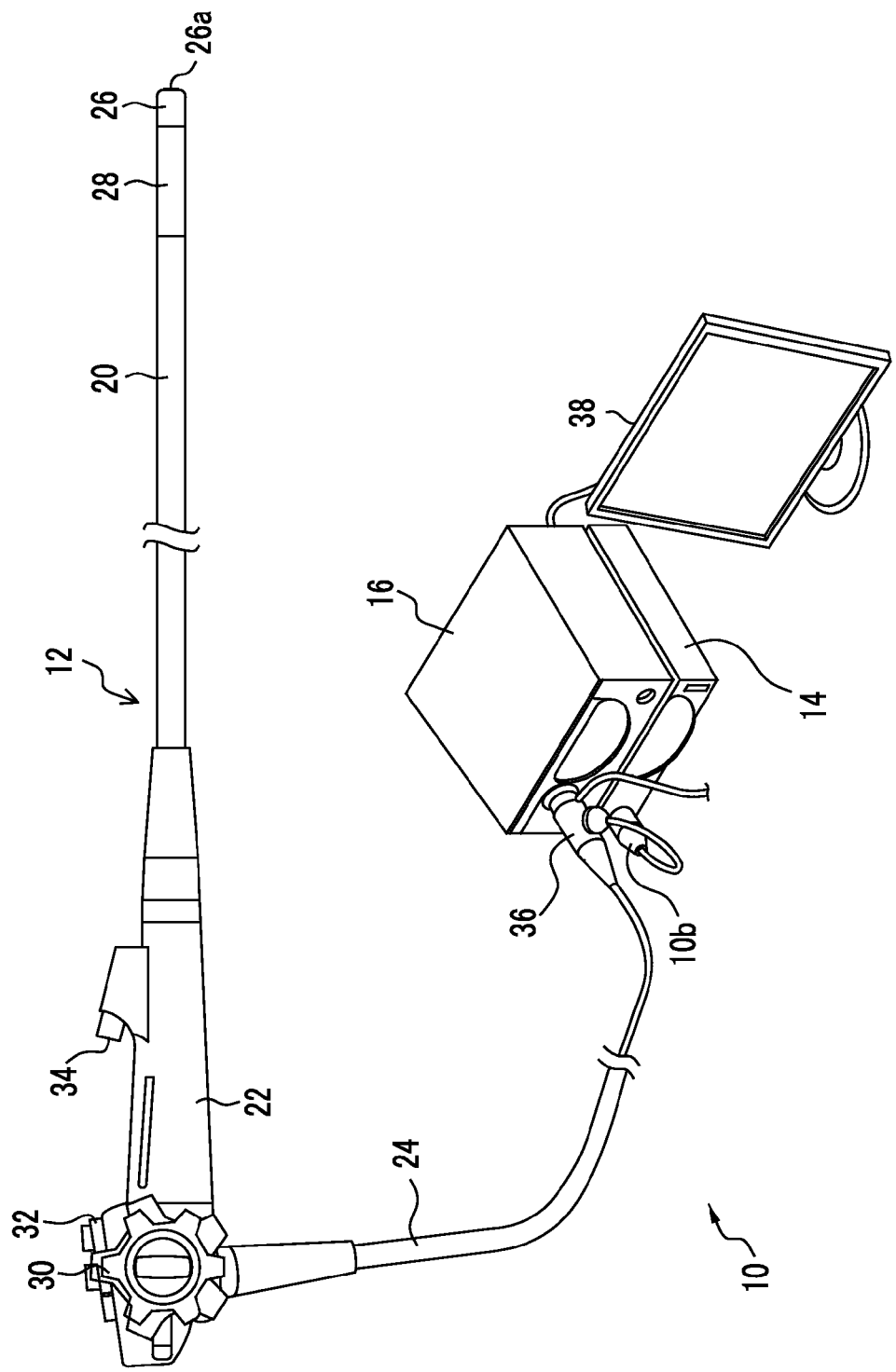
FIG. 1 is a schematic configuration view showing the schematic configuration of an electronic endoscope system related to an embodiment of the invention.

FIG. 1 is a schematic configuration view showing the schematic configuration of an electronic endoscope system related to an embodiment of the present invention. As shown in FIG. 1, an endoscope system 10 of the present embodiment is constituted by an electronic endoscope 12, a processor device 14, a light source device 16, or the like. The electronic endoscope 12 has a flexible insertion part 20 to be inserted into a body cavity of a patient (subject), a manipulating part 22 continuously provided at a proximal end portion of the insertion part 20, a flexible portion 24 connected to the processor device 14 and the light source device 16.

A distal end portion 26 in which a CMOS imaging device (imaging chip) 54 (refer to FIG. 3) for imaging the inside of a body cavity, or the like is built is continuously provided at the distal end of the insertion part 20. A curvable portion 28 in which a plurality of curved pieces are coupled together is provided behind the distal end portion 26. The curvable portion 28 is operated to curve in vertical and horizontal directions as an angle knob 30 provided at the manipulating part 22 is manipulated and a wire provided so as to be inserted into the insertion part 20 is pushed or pulled. This causes the distal end portion 26 to be directed in a desired direction within a body cavity.

A proximal end of the flexible portion 24 is coupled to a connector 36. The connector 36 is of a complex type, and not only the light source device 16 but also the processor device 14 are connected to the connector 36. Although not shown in FIG. 1, an electronic circuit board (designated by reference numeral 130 in FIG. 5) referred to as a scope board is arranged inside the connector 36. The configuration of the scope board will be described below.

The processor device 14 supplies electric power to the electronic endoscope 12 via a cable 68 (refer to FIG. 3) inserted into the flexible portion 24, controls driving of a CMOS imaging device 54, receives imaging signals transmitted via the cable 68 from the CMOS imaging device 54, and performs various signal processing on the received imaging signals to convert the signal into image data. The image data converted by the processor device 14 is displayed as an endoscope image on a monitor 38 (equivalent to a "display device") that is connected by cable to the processor device 14. Additionally, the processor device 14 is electrically connected to the light source device 16 via the connector 36, and controls the operation of the endoscope system 10 in general.

Figure 2:
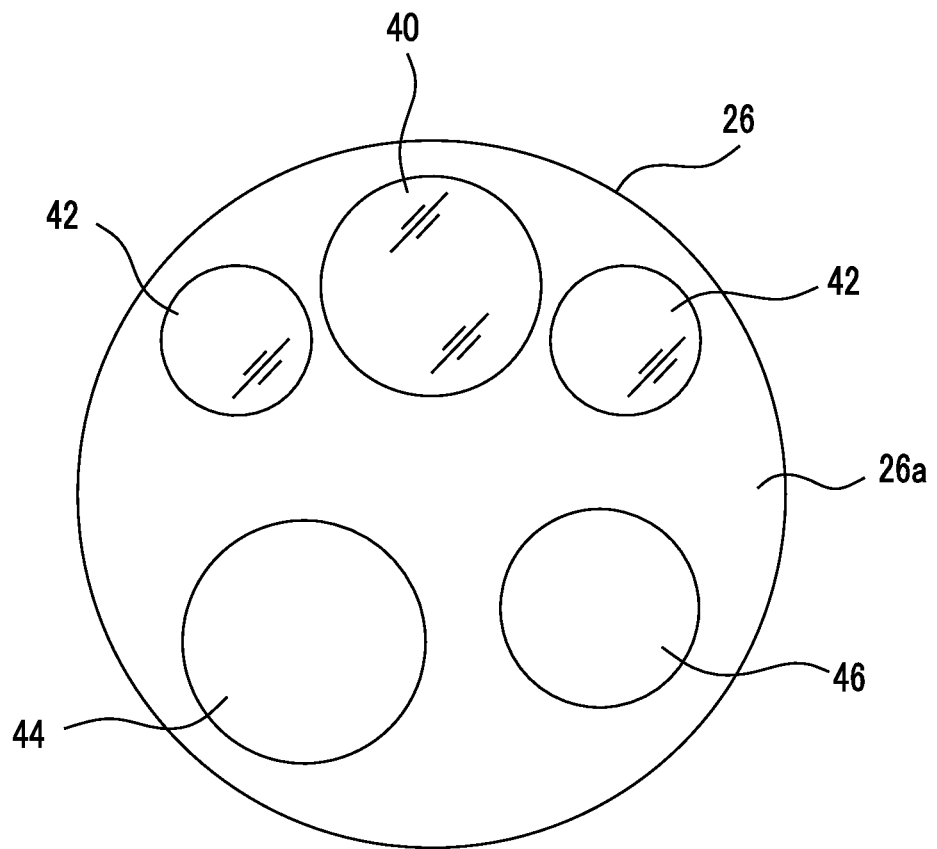
FIG. 2 is a front view showing a distal end portion of an insertion part in an electronic endoscope.

FIG. 2 is a front view showing the distal end portion 26 of the electronic endoscope 12. As shown in FIG. 2, a distal end face 26a of the distal end portion 26 is provided with an observation window 40, illumination windows 42, a forceps outlet 44, and an air and water supply nozzle 46. The observation window 40 is arranged at the center of one side of the distal end portion 26. The illumination windows 42 are arranged at two positions symmetrical with respect to the observation window 40, and irradiate a region to be observed within a body cavity from the light source device 16. The forceps outlet 44 is connected to a forceps channel 70 (refer to FIG. 3) disposed within the insertion part 20, and communicates with a forceps port 34 (refer to FIG. 1) provided in the manipulating part 22. Various treatment tools having an injection needle, a diathermy knife, or the like disposed at the distal end thereof are inserted through the forceps port 34, and distal ends of the various treatment tools are exposed from the forceps outlet 44. The air and water supply nozzle 46 jets washing water or air, which is supplied from an air and water supply device built in the light source device 16, toward the observation window 40 or a body cavity, according to the manipulation of the air and water supply button 32 (refer to FIG. 1) provided at the manipulating part 22.

Figure 3:
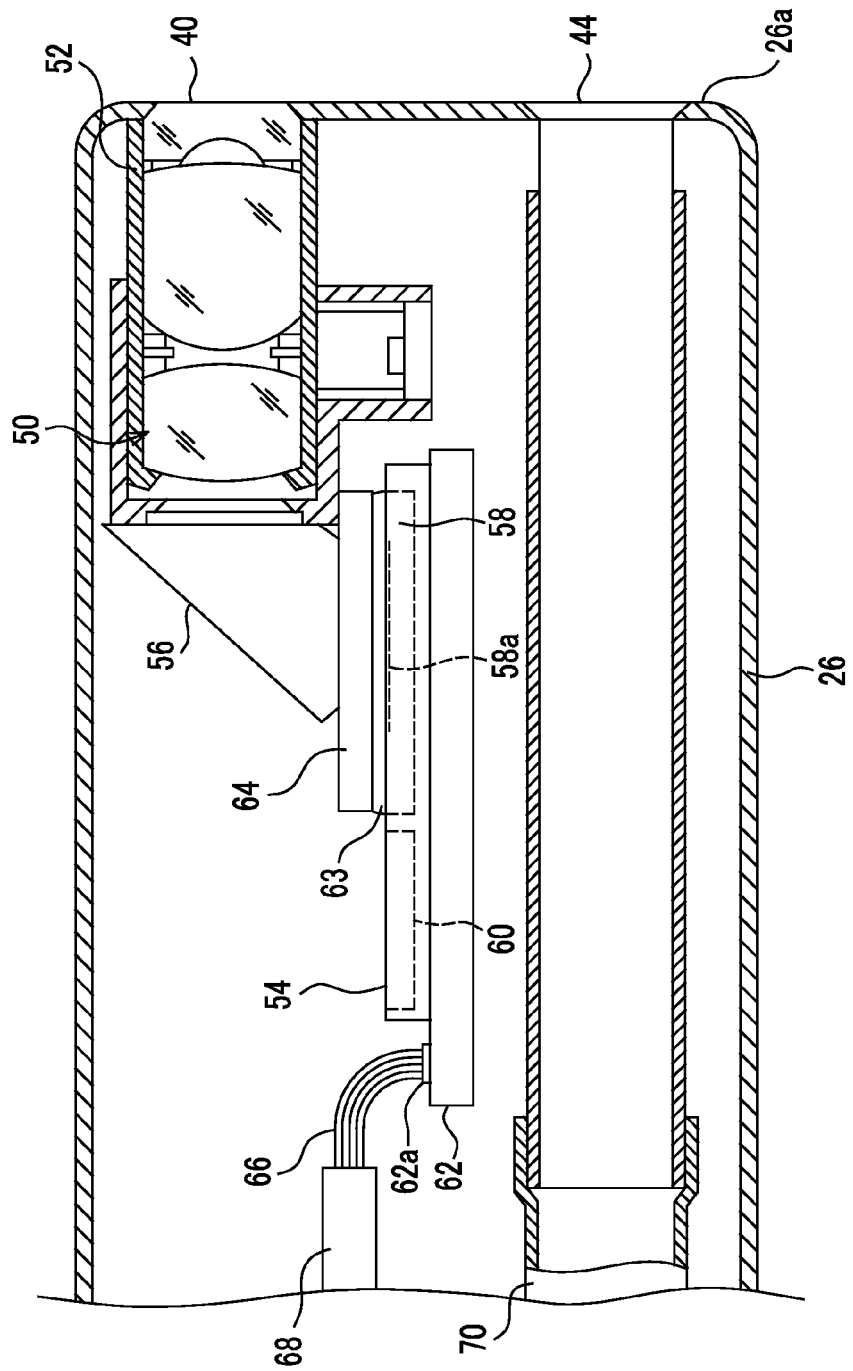
FIG. 3 is a lateral cross-sectional view showing the distal end portion of the insertion part in the electronic endoscope.

FIG. 3 is a lateral cross-sectional view showing the distal end portion 26 of the electronic endoscope 12. As shown in FIG. 3, a lens barrel 52 holding an objective optical system 50 for taking in image light of a region to be observed within a body cavity is disposed at the back of the observation window 40. The lens barrel 52 is attached so that the optical axis of the objective optical system 50 becomes parallel to the central axis of the insertion part 20. A prism 56, which deflects the image light of the region to be observed which has passed through the objective optical system 50 approximately at a right angle and guides the image light toward the CMOS imaging device 54, is connected to a rear end of the lens barrel 52.

The CMOS imaging device 54 is a monolithic semiconductor (so-called CMOS sensor chip) in which a CMOS type solid-state imaging element (hereinafter referred to as a "CMOS sensor") 58, and a peripheral circuit 60 that performs the driving of the CMOS sensor 58 and the input/output of a signal are formed integrally, and is mounted on a supporting substrate 62. An imaging surface 58a of the CMOS sensor 58 is arranged so as to face the emitting surface of the prism 56. A rectangular plate-shaped cover glass 64 is attached onto the imaging surface 58a via a rectangular frame-shaped spacer 63. The CMOS imaging device 54, the spacer 63, and the cover glass 64 are assembled together with adhesive. This protects the imaging surface 58a from entry of dust or the like.

A plurality of input/output terminals 62a are provided side by side in the width direction of the supporting substrate 62 at a rear end portion of the supporting substrate 62 that is provided to extend toward the rear end of the insertion part 20. Signal lines 66 for intermediating exchange of various signals with the processor device 14 via the flexible portion 24 are joined to the input/output terminals 62a, and the input/output terminals 62a are electrically connected to the peripheral circuit 60 in the CMOS imaging device 54 via wiring lines, bonding pads (not shown), or the like that are formed on the supporting substrate 62. The signal lines 66 are packed and inserted into the flexible tubular cable 68. The cable 68 is inserted through the inside of each of the insertion part 20, the manipulating part 22, and the flexible portion 24, and is connected to the connector 36.

Additionally, although illustration is omitted in FIG. 2, illumination parts are provided at the back of the illumination windows 42. An emission end (reference numeral 106a in FIG. 4) of the light guide (reference numeral 106 in FIG. 4), which guides the illumination light from the light source device 16, is arranged at the illumination part. The light guide 106, similarly to the cable 68, is inserted through the inside of each of the insertion part 20, the manipulating part 22, and the flexible portion 24, and an incidence end is connected to the connector 36.

Figure 4:
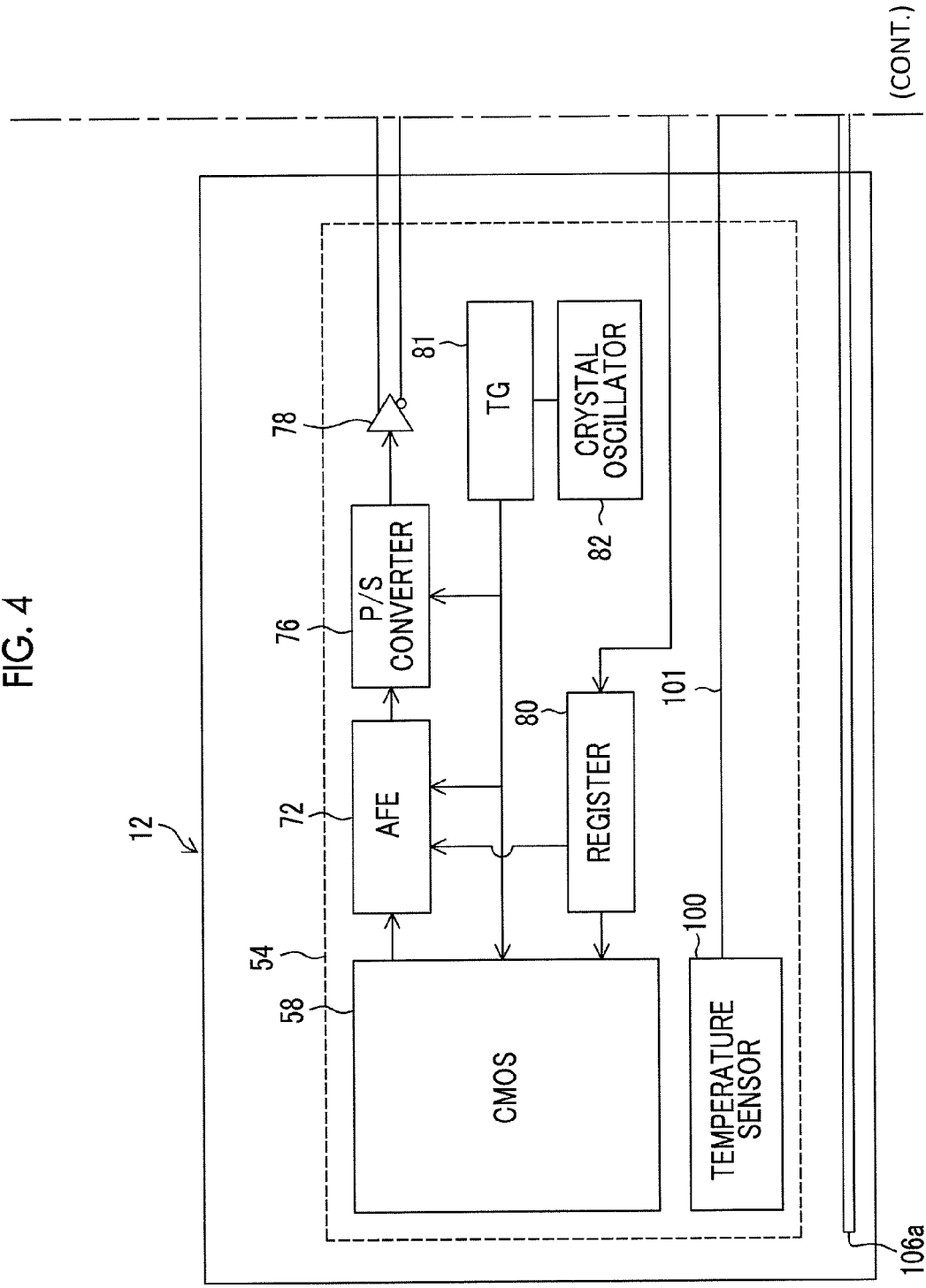
FIG. 4 is a block diagram showing the configuration of the electronic endoscope and a processor device in the endoscope system of this example.
Figure 4:
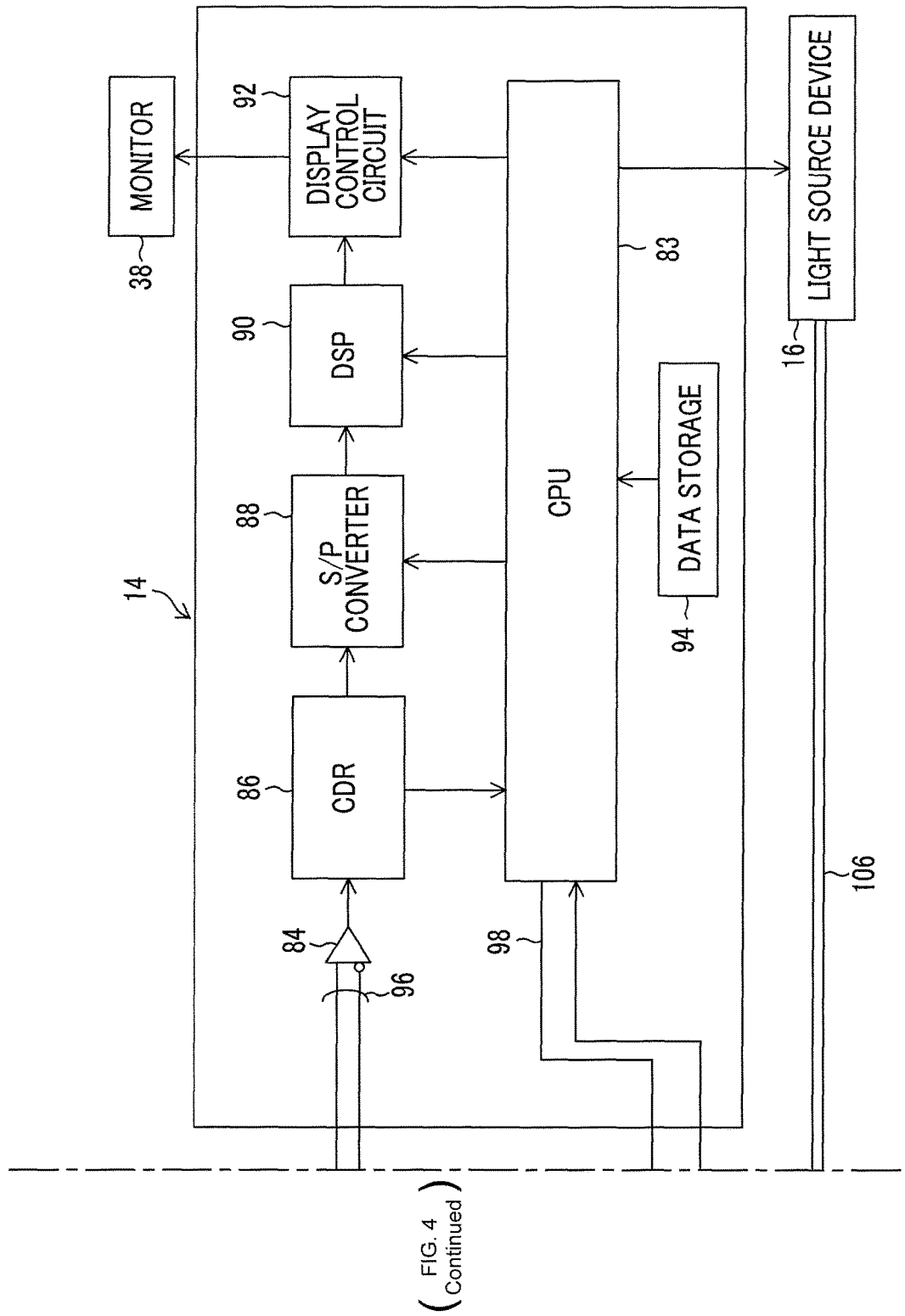

FIG. 4 is a block diagram showing the configuration of the electronic endoscope 12 and the processor device 14 in the endoscope system 10. As shown in FIG. 4, the CMOS imaging device (imaging chip) 54 in which the CMOS sensor 58 and the peripheral circuit 60 (refer to FIG. 3) are formed in the same chip is built in the distal end portion 26 of the electronic endoscope 12 (insertion part 20), and the peripheral circuit 60 is equipped with an analog signal processing circuit (AFE; analog front end) 72, a parallel/serial (P/S) converter 76, an LVDS transmitter 78, a register 80, a timing generator (TG) 81, or the like. Additionally, the CMOS imaging device 54 includes a crystal oscillator 82 for generating clock signals that are required for the driving of the CMOS sensor 58.

The CMOS sensor 58 includes photodiodes that are formed for respective pixels that are arranged in a matrix, a voltage conversion circuit that coverts signal charges stored by the photodiodes into voltage signals, scanning circuits (a vertical-scanning circuit and a horizontal scanning circuit) that specify the addresses (positions) of the pixels that read voltage signals from the voltage conversion circuit, and an output circuit that outputs the voltage signals of the pixels read by the scanning circuits in order.

The AFE 72 is constituted by a correlated double sampling (CDS) circuit, a gain setting circuit (PGA; Programmable Gain Amplifier), and an analog/digital (A/D) converter. The CDS circuit performs correlated double sampling processing on imaging signals including pixel signals sequentially read from the respective pixels of the CMOS sensor 58, and performs rejection of a reset noise made and an amplifier noise arising in the CMOS sensor 58. The PGA amplifies the imaging signals on which noise rejection has been performed by the CDS circuit with a gain (amplification factor) specified from the processor device 14. The A/D converter converts and outputs the imaging signals (analog imaging signals) amplified by the PGA, into digital signals with a predetermined number of bits. The imaging signals (digital imaging signals) that are digitized and output by the A/D converter are input to the P/S converter 76.

The P/S converter 76 converts the imaging signals input from the A/D converter of the AFE 72 into serial signals from parallel signals. The serial signals generated by the P/S converter 76 are input to the LVDS transmitter 78.

The LVDS transmitter 78 outputs the serial signals input from the P/S converter 76 by an LVDS (Low Voltage Differential Signal) transmission system capable of high-speed transmission as differential signals. The differential signals output from the LVDS transmitter 78 are input to the LVDS receiver 84 of the processor device 14 through an LVDS line 96 including two signal lines.

The register 80 is a memory that stores various pieces of control data that determine the processing contents of the respective parts in the CMOS imaging device 54. The control data stored in the register 80 includes various kinds of control information for determining various operation modes (a still image priority mode, a moving image priority mode, a frame rate, or the like) of the CMOS imaging device 54, such as scan modes (full pixel scanning/interlace scanning) of pixels, pixel regions to scan (positions of pixels where scanning starts or ends), and shutter speed (exposure time). The control data is input to the register 80 through a serial line 98 from the processor device 14. The control data input from the processor device 14 is stored in the register 80, and the respective parts of the CMOS imaging device 54 perform various kinds of processing according to register values (that is, the control data input from the processor device 14) stored in the register 80.

The TG 81 generates driving pulses for reading pixel signals from the CMOS sensor 58, on the basis of the clock obtained from the crystal oscillator 82, or synchronizing pulses of the respective parts, such as the AFE 72, and supplies the driving pluses to the respective parts of the CMOS imaging device 54. Then, the respective parts of the CMOS imaging device 54 performs various kinds of processing according to the pulses supplied from the TG 81. The CMOS sensor 58 can collect up the AFE 72 or the like and can collect up the AFE or the like in the same package. Additionally, the CMOS sensor 58 and the crystal oscillator 82 can be housed in the same semiconductor package. This example provides a sensor module in which the CMOS sensor 58 and the AFE 72 are housed in the same semiconductor package. Additionally, the crystal oscillator 82 is constituted as a package that is separate from the package of the CMOS sensor 58, and the crystal oscillator 82 is arranged near the CMOS sensor 58.

Additionally, in the endoscope system 10 of this example, the temperature sensor 100 is arranged inside the distal end portion 26 as a unit that detects the temperature of the distal end portion 26 (refer to FIG. 1) of the insertion part 20 (refer to FIG. 4). For example, a thermistor, a thermal diode, or the like can be used for the temperature sensor 100. The thermistor is a semiconductor element (resistance circuit element) in which electric resistance changes greatly depending on differences in temperature. The thermal diode is an element that measures temperature using the temperature dependency of the voltage drop of a pn-junction. Temperature is obtained from the relationship between voltage and current in a forward direction by allowing a fixed electric current to flow through this element. Such a temperature sensor element can be housed in the same semiconductor package as the CMOS sensor 58 along with the circuit of the AFE 72 or the like.

Otherwise, a temperature sensor IC (for example, CMOS temperature sensor IC) of a package that is separate from the CMOS sensor 58 can be adopted as the temperature sensor 100. As for the temperature sensor IC, a temperature sensor, a constant current circuit, and an operational amplifier or are integrated into a chip.

Figure 5:
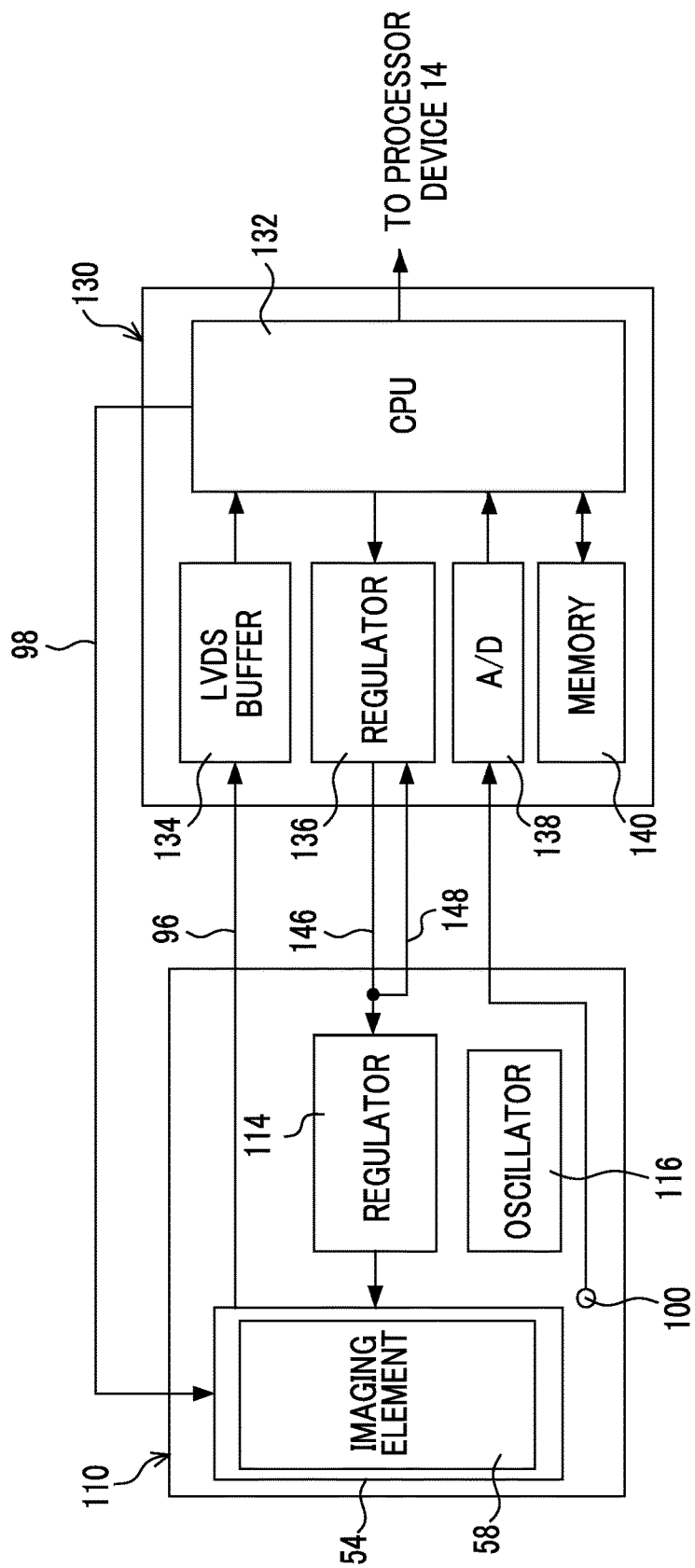
FIG. 5 is a block diagram of main parts showing the internal configuration of the endoscope distal end portion and the configuration of a scope board in a first embodiment.

Signals obtained from the temperature sensor 100 are transmitted to a CPU 83 of the processor device 14 via the scope board (not shown in FIG. 4, reference numeral 130 of FIG. 5). However, a signal transmission unit for transmitting signals (detection signals) from the temperature sensor 100 to the CPU 83 is not limited particularly. For example, an aspect is also possible in which the detection signals of the temperature sensor 100 are sent to the AFE 72, the signal of the temperature sensor 100 along with the image signals are also A/D-converted by the AFE 72, and the image signals and the temperature sensor signal are supplied to the processor device 14 via the LVDS line 96 in combination.

The processor device 14 includes the CPU 83, the LVDS receiver 84, a clock data recovery (CDR) circuit 86, a serial/parallel (S/P) converter 88, an image-processing circuit (DSP) 90, a display control circuit 92, or the like.

The CPU 83 functions as an unit that functions as a control device that controls the respective parts in the processor device 14 and controls light emission and diaphragming (iris) of the light source device 16.

The LVDS receiver 84 performs communication based on the LVDS transmission system, and receives imaging signals (serial signals) transmitted as differential signals from the LVDS transmitter 78. The imaging signals transmitted through the LVDS line 96 are serial signals in which clock signals and image data are mixed. The imaging signals received by the LVDS receiver 84 are input to the S/P converter 88 via the CDR circuit 86.

The CDR circuit 86 detects the phase of the imaging signals serial-transmitted out from the CMOS imaging device 54, and generates extraction clock signals synchronized with the frequency of the imaging signals. By sampling imaging signals by the extraction clock signals, data (retiming data) obtained by retiming the imaging signals by the extraction clock signals is generated.

Data required for various kinds of control by the CPU 83 is stored in a data storage 94. The CPU 83 reads the data from the data storage 94 if necessary, and uses the data for processing.

The S/P converter 88 converts the imaging signals (retiming data) input via the CDR circuit 86 from the LVDS receiver 84 into parallel signals from serial signals, and restores the imaging signals to original imaging signals before the conversion in the P/S converter 76 of the CMOS imaging device 54. The imaging signals converted into the parallel signals by the S/P converter 88 are input to the DSP 90.

The DSP 90 performs color interpolation, color separation, color balance adjustment, gamma correction, image enhancement processing, or the like, on the imaging signals input from the S/P converter 88, and generates image data. The image data on which various kinds of image processing are performed and generated in the DSP 90 is input to the display control circuit 92.

The display control circuit 92 converts the image data input from the DSP 90 into video signals according to signal formats corresponding to the monitor 38 and outputs the image data to the monitor 38.

When the inside of a body cavity is observed by the endoscope system 10 configured as described above, the power sources of the electronic endoscope 12, the processor device 14, the light source device 16, and the monitor 38 are turned on, the insertion part 20 of the electronic endoscope 12 is inserted into the body cavity, and an image within the body cavity captured by the CMOS imaging device 54 is observed with the monitor 38 while the inside of the body cavity is illuminated with the illumination light from the light source device 16.

In that case, control data for controlling the respective parts of the CMOS imaging device 54 is generated in the CPU 83 of the processor device 14. The generated control data is transmitted to the electronic endoscope 12 through the serial line 98, and is stored in the register 80 of the CMOS imaging device 54. The respective parts of the CMOS imaging device 54 perform various kinds of processing according to register values (control data) stored in the register 80.

After the imaging signals generated by the CMOS sensor 58 are subjected to various kinds of processing by the AFE 72, the imaging signals are converted into serial signals from parallel signals by the P/S converter 76, and are transmitted to the processor device 14 as differential signals according to the LVDS transmission system from the LVDS transmitter 78.

In the processor device 14, the imaging signals received by the LVDS receiver 84 are converted into original parallel signals by the S/P converter 88. In the DSP 90, various kinds of signal processing are performed on the input imaging signals, generating image data. The image data generated by the DSP 90 is input to the display control circuit 92. In the display control circuit 92, conversion processing corresponding to the display format of the monitor 38 is performed on the input image data, generating video signals. The video signals generated by the display control circuit 92 are output to the monitor 38. This allows the image data to be displayed as an endoscope image on the monitor 38.

Configuration of Scope Board

FIG. 5 is a block diagram of main parts showing the internal configuration of the endoscope distal end portion and the configuration of the scope board in the first embodiment.

In FIG. 5, elements that are the same or similar to the configuration described in FIG. 4 are designated by the same reference numerals. The scope board 130 is arranged inside the connector described with reference numeral 36 of FIG. 1. A circuit group that relays delivery of signals between the electronic endoscope 12 and the processor device 14, and functions as a relay board is mounted on the scope board 130. The scope board 130 is equivalent to a "second circuit part".

A distal end circuit part 110 (equivalent to a "first circuit part") arranged at the endoscope distal end portion includes the CMOS imaging device 54 including the CMOS sensor 58 and its peripheral circuit, the temperature sensor 100, a first regulator 114 as a power circuit, and an oscillator 116 that generate clock signals. The first regulator 114 is a voltage conversion device that generates a plurality of types of predetermined voltages (for example, three types of direct current voltages with different voltage values) supplied to the respective circuit parts of the CMOS imaging device 54, and functions as a supply source of power to the respective circuit parts within the endoscope distal end portion 126.

The oscillator 116 is equivalent to the crystal oscillator 82 described in FIG. 4, and generates clock signals required for the driving of the CMOS sensor 58.

The scope board 130 is mounted with a CPU 132, an LVDS buffer 134, a second regulator 136, an A/D converter 138, and a memory 140. The CPU 132 communicates with the CMOS imaging device 54 of the distal end portion 26 via the serial line 98. Additionally, the CPU 132 communicates with the CPU 83 (refer to FIG. 1) of the processor device 14, and controls the endoscope system 10 in cooperation with the CPU 83.

The image data output from the CMOS imaging device 54 is sent to the LVDS buffer 134 via the LVDS line 96. Serial data sent out from CMOS imaging device 54 is once buffered by the LVDS buffer 134, and then transferred to the processor device 14. Additionally, although not shown, the scope board 130 detects various switches of the manipulating part 22 described in FIG. 1, and includes a circuit that performs communication of switch signals (manipulate signals) with the processor device 14.

Specific information of the scope is stored in the memory 140. The electronic endoscope (scope) holds individual pieces of data in the memory 140 for every model, and performs optimal control for an instrument on the basis of this information. By adopting such a configuration, it is possible to commonly use the processor device 14 and the light source device 16 regarding various variations of the scope.

The second regulator 136 as a power circuit for supplying electric power to the first regulator 114 of the endoscope distal end portion is provided within the scope board 130. Power of a predetermined voltage is supplied to the first regulator 114 of the endoscope distal end portion via a power supply line 146 from the second regulator 136. The voltage of a power source input terminal of the first regulator 114 is fed back to the second regulator 136 via a feedback circuit (return line) 148, and the output of the second regulator 136 is controlled automatically. A predetermined voltage (for example, 3 V) is supplied to the first regulator 114 of the endoscope distal end portion by such feedback control.

According to such a configuration, even in a case where the model of the scope (electronic endoscope 12) is changed, electric power of a proper voltage value is supplied to the first regulator 114 of the distal end portion by the voltage feedback control function between the first regulator 114 and the second regulator 136 in the electronic endoscope of each model.

After signals obtained from the temperature sensor 100 are converted into digital signals from analog signals by the A/D converter 138, the signals are input to the CPU 132 of the scope board 130.

If a temperature abnormality of the endoscope distal end portion 26 is detected by the temperature sensor 100, the CPU 132 controls the second regulator 136 to stop the supply of electric power from the second regulator 136. Specifically, the CPU 132 sets an enable signal of the second regulator 136 to "OFF", bringing the second regulator 136 into non-operation (output off), and stops the supply of a power voltage to the first regulator 114 of the endoscope distal end portion. As a result, the output of the first regulator 114 is also stopped, and the supply of power to the CMOS imaging device 54 is cut off.

According to such a configuration, if a temperature abnormality of the distal end portion is detected, the supply of electric power to the distal end portion is stopped, and a temperature rise is suppressed, so that the distal end temperature can be prevented from reaching a temperature higher than an allowable temperature. Additionally, when the CPU 132 of the scope board 130 performs the control of stopping the output of the second regulator 136 with this abnormality detection, an aspect is preferable in which the control of performing the communication from the CPU 132 to the processor device 14 side to stop the light emission of the light source device 16 or reduce the amount of light emission.

Second Embodiment

Figure 6:
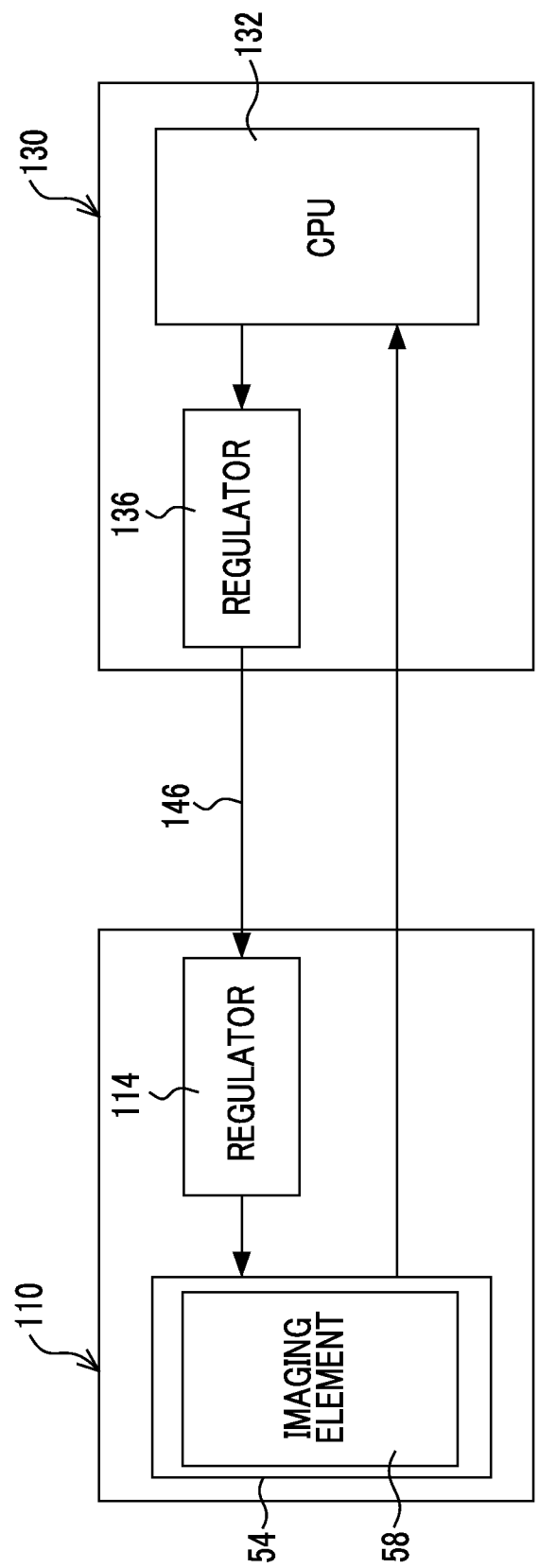
FIG. 6 is a block diagram of main parts of a second embodiment.

FIG. 6 is a block diagram of main parts of a second embodiment. In FIG. 6, elements that are the same or similar to the example described in FIG. 5 are designated by the same reference numerals, and the description thereof is omitted. In addition, in order to simplify illustration in FIG. 6, the description of the oscillator 116, the LVDS buffer 134, the A/D converter 138, the memory 140, and the feedback circuit 148, which are described in FIG. 5, is omitted. This is also the same in FIGS. 7 to 9.

The second embodiment of FIG. 6 is that a thermal diode (not shown) is assembled into the CMOS imaging device 54, instead of the temperature sensor 100 (thermistor) of FIG. 5. If abnormal heat generation is detected within the imaging element module (CMOS imaging device 54) in which a temperature detecting element is assembled, the detection information is notified to the CPU 132 within the scope board 130. The CPU 132 controls the second regulator 136 to stop the output of the second regulator 136, on the basis of a temperature abnormality detection signal obtained from the distal end circuit part 110. Specifically, the CPU 132 sets an enable signal of the second regulator 136 to "OFF", bringing the second regulator 136 into non-operation (output off), and stops the supply of a power voltage to the first regulator 114 of the endoscope distal end portion. As a result, the output of the first regulator 114 is also stopped, and the supply of power to the CMOS imaging device 54 is cut off. Moreover, the CPU 132 preferably performs the control of performing notification to the CPU 83 of the processor device 14, to stop the light emission of the light source device 16 or reduce the amount of light emission.

Third Embodiment

Figure 7:
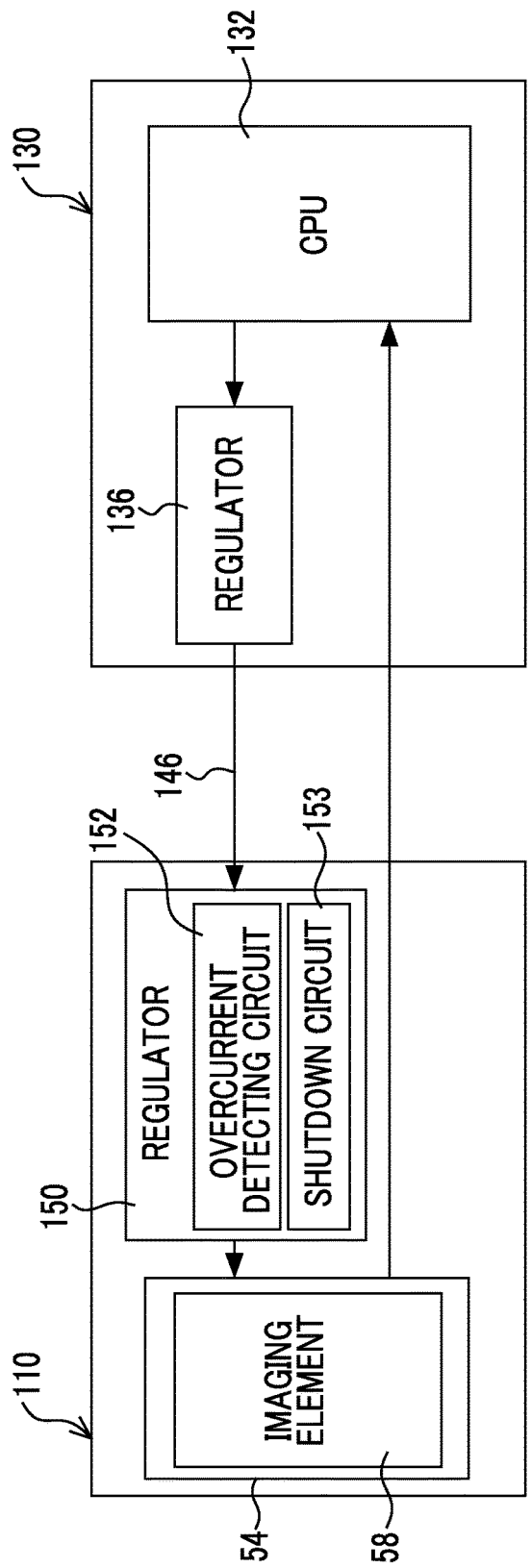
FIG. 7 is a block diagram of main parts of a third embodiment.

FIG. 7 is a block diagram of main parts of a third embodiment. In FIG. 7, elements that are the same or similar to the example described in FIGS. 5 and 6 are designated by the same reference numerals, and the description thereof is omitted.

The third embodiment shown in FIG. 7 has a configuration in which elements for detecting temperature, such as the temperature sensor 100 described in FIG. 5 or the thermal diode described in FIG. 6, are not provided. While the configuration in which the temperature detecting element is omitted is adopted, the first regulator 150 to be mounted on the endoscope distal end portion includes an overcurrent detecting circuit 152, and a shutdown circuit 154 that performs a self-shutdown when overcurrent is detected. An overcurrent protection circuit is constituted by the combination of the overcurrent detecting circuit 152 and the shutdown circuit 154. That is, an overcurrent protection circuit, which monitors the amount of current that is output and which stops output automatically when an output exceeding the amount of allowable current is detected, is assembled into the first regulator 150.

According to such a configuration, in a case where an overcurrent occurs in the endoscope distal end portion due to some causes, such as a circuit failure, supply of electric power is cut off by the self-shutdown function of the first regulator 150. This suppresses the temperature rise of the distal end portion. Additionally, since supply of electric power is stopped quickly after overcurrent detection, an abnormal state is not left for a long time, and spreading of failure damage to an electronic circuit can be prevented.

Fourth Embodiment

Figure 8:
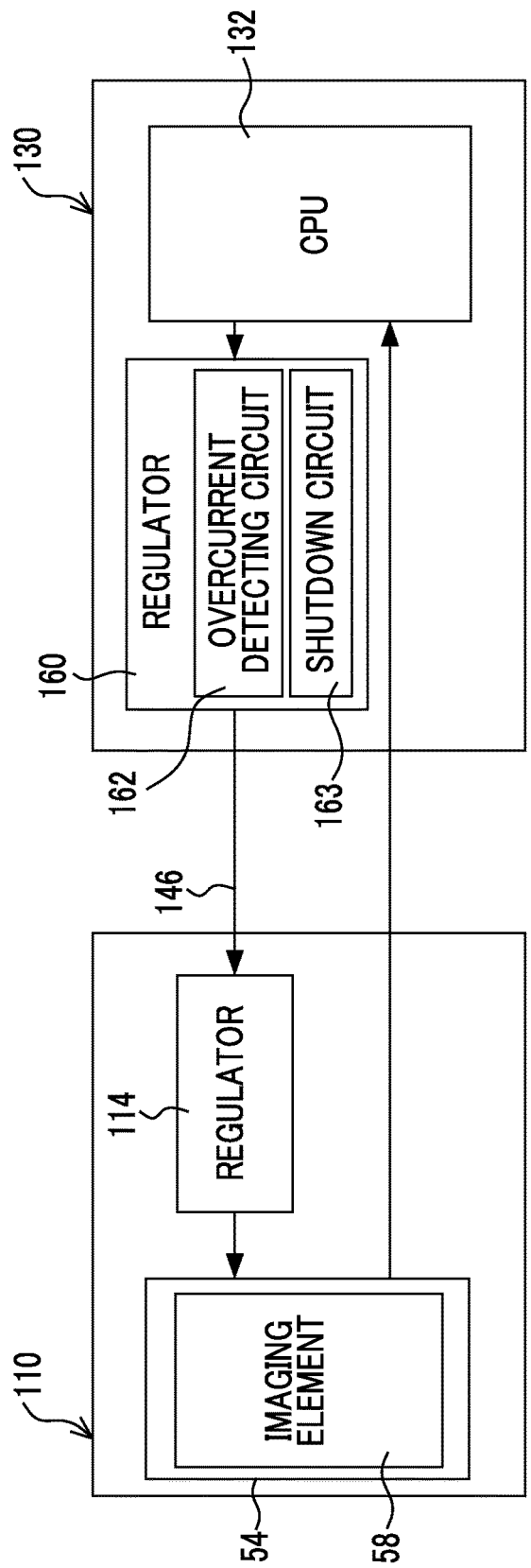
FIG. 8 is a block diagram of main parts of a fourth embodiment.

FIG. 8 is a block diagram of main parts of a fourth embodiment. In FIG. 8, elements that are the same or similar to the example described in FIGS. 5 and 6 are designated by the same reference numerals, and the description thereof is omitted.

The fourth embodiment shown in FIG. 8 has a configuration in which elements for detecting temperature, such as the temperature sensor 100 described in FIG. 5 and the thermal diode described in FIG. 6, are not provided. While the configuration in which the temperature detecting element is omitted is adopted, the second regulator 160 to be mounted on the scope board 130 includes an overcurrent detecting circuit 162, and a shutdown circuit 164 that perform a self-shutdown when overcurrent is detected. An overcurrent protection circuit is constituted by the combination of the overcurrent detecting unit 162 and the shutdown circuit 164. That is, an overcurrent protection circuit, which monitors the amount of current that is output and which stops output automatically when an output exceeding the amount of allowable current is detected, is assembled into the second regulator 160.

According to such a configuration, in a case where an overcurrent occurs in the endoscope distal end portion due to some causes, such as a circuit failure, since the amount of current that the second regulator 160 of the scope board 130 outputs is also increased, the overcurrent protection of the second regulator 160 works, and the supply of electric power to the endoscope distal end portion is cut off by the self-shutdown function. As a result, the output of the first regulator 114 is also stopped. This suppresses the temperature rise of the distal end portion. Additionally, since supply of electric power is stopped quickly after overcurrent detection, an abnormal state is not left for a long time, and spreading of failure damage to an electronic circuit can be prevented.

Fifth Embodiment

Figure 9:
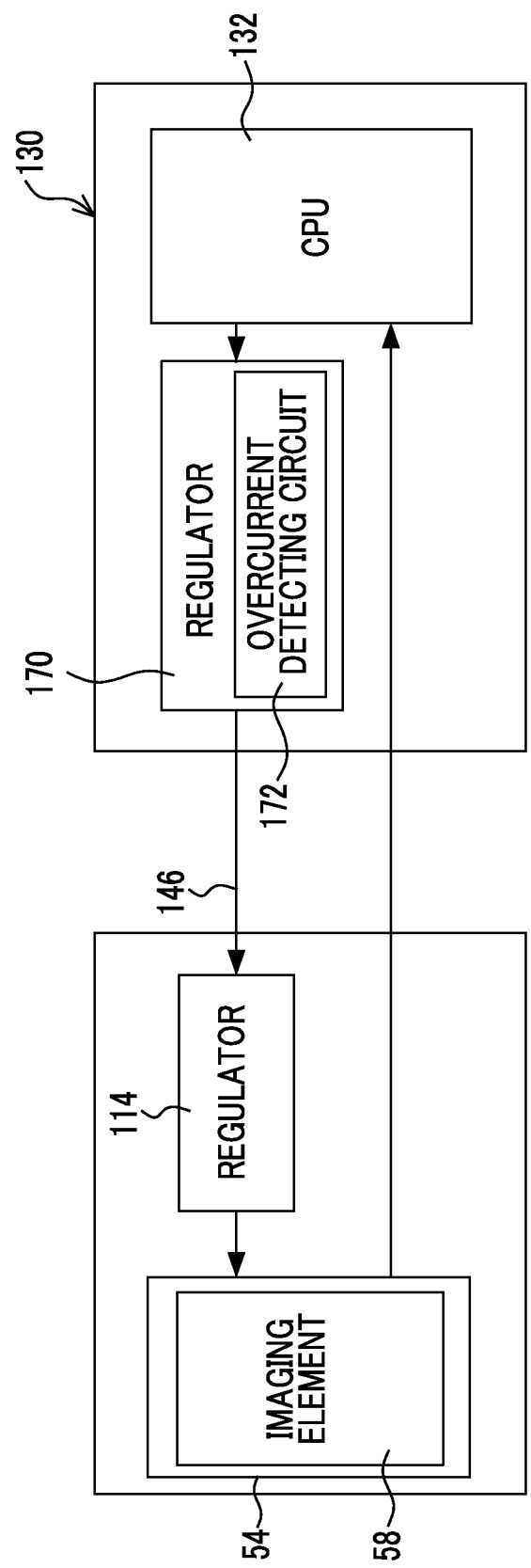
FIG. 9 is a block diagram of main parts of a fifth embodiment.

FIG. 9 is a block diagram of main parts of a fifth embodiment. In FIG. 9, elements that are the same or similar to the example described in FIGS. 5 and 6 are designated by the same reference numerals, and the description thereof is omitted.

The fifth embodiment shown in FIG. 9 has a configuration in which elements for detecting temperature, such as the temperature sensor 100 described in FIG. 5 and the thermal diode described in FIG. 6, are not provided. While the configuration in which the temperature detecting element is omitted is adopted, the second regulator 170 to be mounted on the scope board 130 includes an overcurrent detecting circuit 172, and a circuit that notifies information to the CPU 132 when overcurrent is detected. That is, the second regulator 170 has a function of monitoring the amount of current that is output, and notifying information to the CPU 132 when an output exceeding the amount of allowable current is detected.

According to such a configuration, in a case where an overcurrent occurs in the endoscope distal end portion due to some causes, such as a circuit failure, since the amount of current that the second regulator 170 of the scope board 130 outputs is also increased, overcurrent is detected and the message is notified to the CPU 132, by the overcurrent detection function of the second regulator 170. The CPU 132 receives this signal to control the second regulator 170 to stop the output of the second regulator 170. Specifically, the CPU 132 sets an enable signal of the second regulator 170 to "OFF", bringing the second regulator 170 into non-operation (output off), and stops the supply of a power voltage to the first regulator 114 of the endoscope distal end portion. As a result, the output of the first regulator 114 is also stopped, and the supply of power to the CMOS imaging device 54 is cut off. This suppresses the temperature rise of the distal end portion. Additionally, since supply of electric power is stopped quickly after overcurrent detection, an abnormal state is not left for a long time, and spreading of failure damage to an electronic circuit can be prevented.

Appropriate Combination of Respective Embodiments of First to Fifth Embodiments

The configurations of the respective embodiments described in the first to fifth embodiments can be combined appropriately. For example, as the first regulator 114 of FIGS. 5 and 6, it is possible to use a regulator with an overcurrent protection function (reference numeral 150). Additionally, even in the embodiment described in FIGS. 7 and 8, it is possible to perform the control of performing the communication from the CPU 132 to the processor device 14 to stop the light emission of the light source device 16 or reduce the amount of light emission at the time of cutoff of power supply when overcurrent is detected.

Light-Emitting Source of Light Source Device 16

As the light-emitting source of the light source device 16, a laser light source may be adopted, lamp light sources, such as a xenon tube, may be adopted, or a light emission diode (LED) may be adopted. In the laser light source or the LED light source, adjustment of the amount of light emission or control of pulse light emission is relatively easy. On the other hand, in the xenon light source or the like, adjustment of the amount of light emission of the light source itself is difficult. Therefore, the amount of illumination light may be adjusted using a aperture mechanism or the like.

Modification 1

In the above-described embodiments, the configuration in which illumination light is guided to the endoscope distal end portion via the light guide (optical fiber or the like) from the light source device 16 has been illustrated. Instead of this aspect, a configuration is also possible in which a light emission source, such as a light emission diode (LED), is arranged at the endoscope distal end portion in combination with this configuration. In this case, power of the LED built in the endoscope distal end portion is supplied from the first regulator 114 (or 150), and an illumination light can also be turned off by the stopping of output of the first regulator 114 (or 150).

Modification 2

Instead of the aspects in which temperature detecting elements, such as the temperature sensor 100 described in the above first embodiment and the thermal diode described in the second embodiment, are used, it is also possible to detect the temperature of the distal end portion 26, using the frequency temperature characteristics of the crystal oscillator 82 arranged at the distal end portion 26. In this case, the temperature sensor 100 can be omitted.

Since the crystal oscillator 82 has the property that the oscillation frequency thereof fluctuates depending on temperature, temperature can be estimated from the frequency. Specifically, for example, in the processor device 14, the oscillation frequency of the crystal oscillator 82 of the endoscope insertion part is confirmed, for example, by counting pixel clocks (clocks of pixel units) of image signals on the basis of clock signals extracted by the CDR circuit 86, or measuring frame periods from image signals or the like. Also, the temperature of the distal end portion 26 can be estimated from correlation data (look-up table or the like) that defines the relationship between the temperature stored in advance in the data storage 94, and the oscillation frequency.

Modification 3

In the above-described embodiments, the CMOS sensor 58 is used as the solid-state imaging element. However, the scope of application of the present invention is not limited to this. As compared to the CCD sensor, the CMOS sensor can be driven at a low voltage, and easily cope with demands for increase in the number of pixels and high-speed reading. Additionally, manufacture of the sensor module is easy. However, when the present invention is carried out, a configuration is also possible in which other types of imaging elements, such as the CCD type solid-state imaging element (CCD sensor), is adopted as well as the CMOS sensor.

Modification 4

Although the example in which the scope board 130 is arranged within the connector 36 (refer to FIG. 1) of the flexible portion 24 has been described in the above-described embodiments, the arrangement place of the scope board 130 is not limited to this example. For example, a configuration is also possible in which the scope board is arranged at a separate connector portion (connector of a portion coupled with the processor device 14) connected to the connector 36. Otherwise, a form in which the scope board is arranged at the manipulating part 22 (refer to FIG. 1) of the electronic endoscope 12 is also considered.

Although the endoscope system and its control method of the present invention have been described in detail above, the present invention is not limited to the embodiments described above, and it is needless to say that various improvements and modifications may be performed without departing from the scope of the present invention. A number of modifications can be made by those having ordinary knowledge in the field concerned with the technical idea of the present invention.

What is claimed is:

1. An electronic endoscope apparatus comprising:
an imaging device built in a distal end portion of an endoscope insertion part, and having a solid-state imaging element that images a region to be observed;
a first regulator arranged within the distal end portion along with the imaging device, the first regulator receiving power of a first predetermined voltage and supplying electric power of a plurality of required voltages to respective parts of the imaging device;
a cable including signal lines that transmit signals obtained from the imaging device and a power supply line that supplies electric power to the first regulator;
a second circuit part electrically connected to a first circuit part including the imaging device and the first regulator within the distal end portion, via the cable;
a second regulator mounted on the second circuit part and connected to the first regulator via the power supply line, the second regulator supplying electric power of the first predetermined voltage to the first regulator;
a sensor that detects a temperature abnormality in the distal end portion,
wherein a temperature detecting unit is provided within the distal end portion as the sensor; and
a power supply stop processor that stops the output of the plurality of required voltages from the first regulator when an abnormality is detected by stopping the second regulator from supplying the first predetermined voltage to the first regulator.

2. The electronic endoscope apparatus according to claim 1, wherein the second regulator supplying electric power to the first circuit part other than the first regulator after the output from the first regulator is stopped.

3. The electronic endoscope apparatus according to claim 1, wherein the second circuit part is arranged at a connector portion formed at the end portion of the cable opposite to the first circuit part.

4. The electronic endoscope apparatus according to claim 2, wherein the second circuit part is arranged at a connector portion formed at the end portion of the cable opposite to the first circuit part.

5. The electronic endoscope apparatus according to claim 1, further comprising a feedback circuit that returns an input voltage, which is supplied to the first regulator via the power supply line from the second regulator, to the second regulator.

6. The electronic endoscope apparatus according to claim 2, further comprising a feedback circuit that returns an input voltage, which is supplied to the first regulator via the power supply line from the second regulator, to the second regulator.

7. The electronic endoscope apparatus according to Claim 1, wherein the solid-state imaging element is a CMOS type solid-state imaging element.

8. The electronic endoscope apparatus according to claim 2, wherein the solid-state imaging element is a CMOS type solid-state imaging element.

9. An electronic endoscope system comprising:
an electronic endoscope apparatus having an imaging device, having a solid-state imaging element that images a region to be observed, built in a distal end portion of an endoscope insertion part;

a processor device that performs signal processing on imaging signals output from the imaging device of the electronic endoscope apparatus; and a light source for illumination that generates illumination light to be irradiated to a region to be observed from an illumination window provided at a distal end face of the endoscope insertion part, wherein the electronic endoscope apparatus includes:

a first regulator arranged within the distal end portion along with the imaging device, the first regulator receiving power of a first predetermined voltage and supplying electric power of a plurality of required voltages to respective parts of the imaging device;

a cable including signal lines that transmit signals obtained from the imaging device and a power supply line that supplies electric power to the first regulator;

a second circuit part electrically connected to a first circuit part including the imaging device and the first regulator within the distal end portion via the cable;

a second regulator mounted on the second circuit part and connected to the first regulator via the power supply line, the second regulator supplying electric power of the first predetermined voltage to the first regulator;

a sensor that detects a temperature abnormality in the distal end portion, wherein a temperature detecting unit is provided within the distal end portion as the sensor; and a power supply stop processor that stops the output of the plurality of required voltages from the first regulator when an abnormality is detected by stopping the second regulator from supplying the first predetermined voltage to the first regulator.

10. The electronic endoscope system according to claim 9, wherein the second circuit part is arranged at a connector portion that detachably couples the electronic endoscope to the light source for illumination together.

* * * * *